US010392361B2

United States Patent
Bartoli et al.

(10) Patent No.: US 10,392,361 B2
(45) Date of Patent: Aug. 27, 2019

(54) PROCESS FOR THE SYNTHESIS OF INTERMEDIATES OF NEBIVOLOL

(71) Applicant: Menarini International Operations Luxembourg S.A., Luxembourg (LU)

(72) Inventors: Sandra Bartoli, Pisa (IT); Serena Mannucci, Pisa (IT); Alessio Griselli, Pisa (IT); Alessio Stefanini, Pisa (IT)

(73) Assignee: Menarini International Operations Luxembourg S.A., Luxembourg (LU)

( * ) Notice: Subject to any disclaimer, the term of this patent is extended or adjusted under 35 U.S.C. 154(b) by 0 days.

(21) Appl. No.: 16/071,741

(22) PCT Filed: Jan. 23, 2017

(86) PCT No.: PCT/IB2017/050332
§ 371 (c)(1),
(2) Date: Jul. 20, 2018

(87) PCT Pub. No.: WO2017/125900
PCT Pub. Date: Jul. 27, 2017

(65) Prior Publication Data
US 2019/0031636 A1 Jan. 31, 2019

(30) Foreign Application Priority Data

Jan. 21, 2016 (IT) .................. 102016000005775

(51) Int. Cl.
*C07D 311/58* (2006.01)
*C07D 407/04* (2006.01)

(52) U.S. Cl.
CPC .......... *C07D 311/58* (2013.01); *C07D 407/04* (2013.01)

(58) Field of Classification Search
CPC .................. C07D 311/58; C07D 407/04
See application file for complete search history.

(56) References Cited

U.S. PATENT DOCUMENTS

| 5,929,284 A | 7/1999 | Nishiyama et al. | |
|---|---|---|---|
| 2007/0149612 A1* | 6/2007 | Bader .................. | C07D 311/58 514/456 |

FOREIGN PATENT DOCUMENTS

| CN | 102190647 A | 9/2011 |
|---|---|---|
| WO | WO 2008040528 A2 | 4/2008 |
| WO | WO 2010034927 A1 | 4/2010 |
| WO | WO 2012095707 A1 | 7/2012 |

OTHER PUBLICATIONS

International Search Report and Written Opinion issued in International Patent Application No. PCT/IB2017/050332 dated Mar. 13, 2017.

* cited by examiner

*Primary Examiner* — Noble E Jarrell
(74) *Attorney, Agent, or Firm* — Arent Fox LLP

(57) ABSTRACT

The present invention relates to a novel process for the synthesis of the intermediate compounds constituted by chromanyl haloketones of formula III and 6-fluoro-2-(oxiran-2-yl)chromans of formula I.
The intermediates thus obtained can be used for the synthesis of Nebivolol.

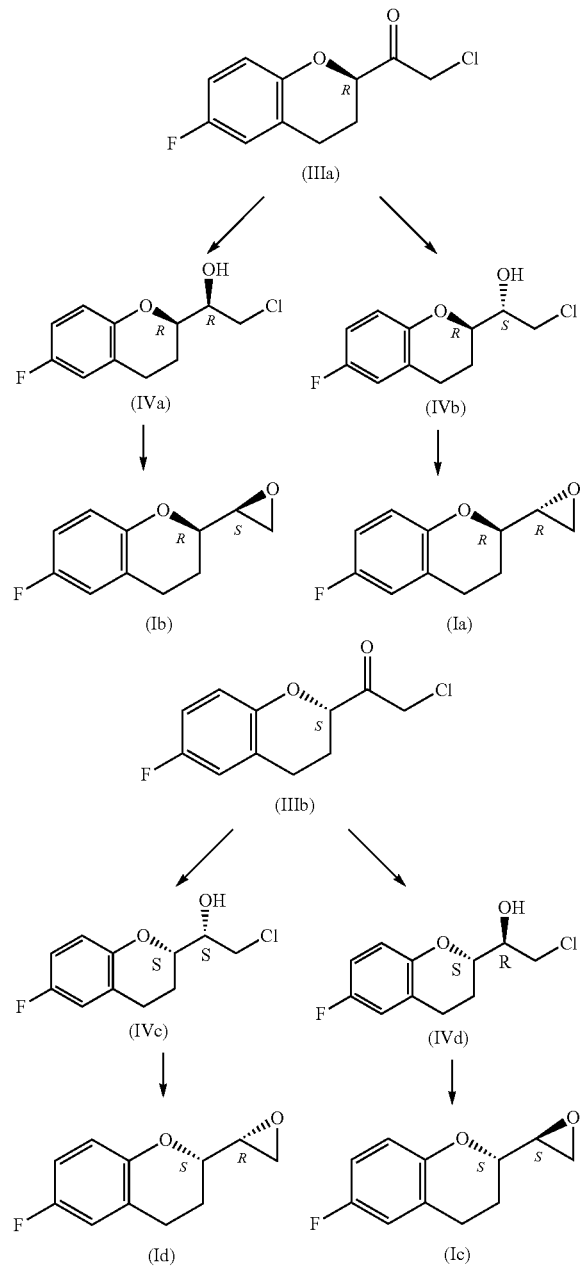

22 Claims, No Drawings

PROCESS FOR THE SYNTHESIS OF INTERMEDIATES OF NEBIVOLOL

CROSS-REFERENCE TO RELATED APPLICATION

This application is a 35 U.S.C. § 371 National Phase of PCT Application No. PCT/IB2017/050332 filed Jan. 23, 2017 which claims priority to IT Application No. 102016000005775 filed Jan. 21, 2016. The disclosure of these prior applications are hereby incorporated by reference herein.

FIELD OF THE INVENTION

The present invention relates to a novel process for the synthesis of chromanyl haloketone and oxiranylchroman compounds, which are useful as intermediates in the synthesis of Nebivolol.

PRIOR ART

Nebivolol is a racemic mixture of the two enantiomers [2S[2R[R[R]]]] α,α'-[imino-bis (methylene)] bis[6-fluoro-chroman-2-methanol] and [2R[2S[S[S]]]] α,α'-[imino-bis (methylene)] bis[6-fluoro -chroman-2-methanol] (FIG. 2).

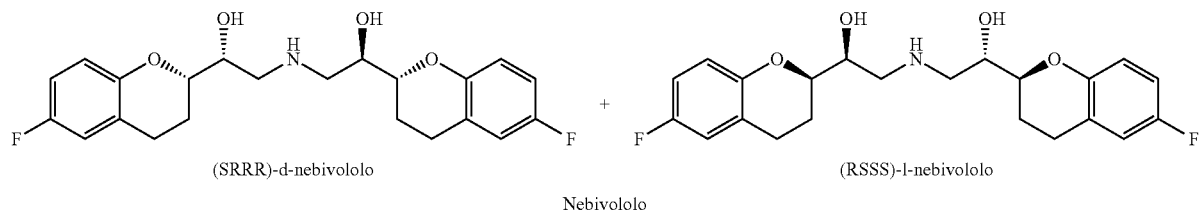 [SMILES: O[C@H](CNC[C@@H](O)[C@H]1CCc2cc(F)ccc2O1)[C@@H]1CCc2cc(F)ccc2O1 ; O[C@@H](CNC[C@H](O)[C@H]1CCc2cc(F)ccc2O1)[C@@H]1CCc2cc(F)ccc2O1]

Nebivololo

The fact that the molecule of Nebivolol contains 4 asymmetric centers, from which, in theory, 16 possible stereoisomers can originate, reduced to 10 due to the symmetry of the molecule, explains the complexity of the structure thereof and the many synthetic approaches developed for the preparation thereof.

The epoxide (I), as a key intermediate in the synthesis of Nebivolol, has been the subject of many synthetic approaches developed for the preparation thereof.

EP0334429 reports the synthesis of the epoxide 6-fluoro-2-(oxiran-2-yl)chroman in the form of the separate diastereomers RS and SR from an ester of chroman carboxylic acid in accordance with a method widely reported in the literature for obtaining carboxylic ester epoxides. The ester of 6-fluoro-chroman carboxylic acid, after resolution of the racemic form into the two enantiomers with (+)-dehydroabietylamine, is reduced at low temperature with diisobutyl aluminium hydride to the corresponding aldehyde, which is in turn converted into the epoxide by reaction with sodium hydride and trimethylsulfonium iodide in dimethylsulfoxide. The following synthetic scheme (Scheme) describes the conversion of the acid R.

Scheme 1

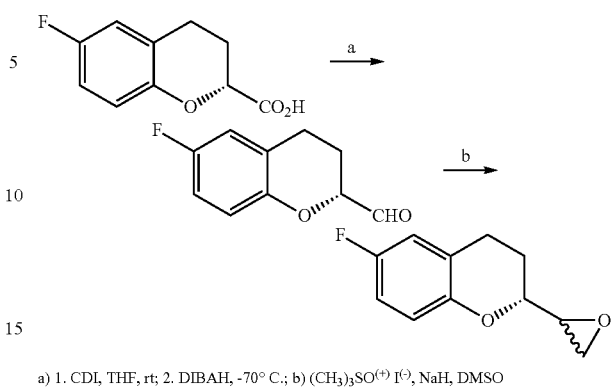

a) 1. CDI, THF, rt; 2. DIBAH, -70° C.; b) (CH₃)₃SO⁽⁺⁾ I⁽⁻⁾, NaH, DMSO

The obtained 6-fluoro-chromanyl aldehyde is not particularly stable and is prone to racemization if it is prepared in optically active form.

EP1803715 (Cimex) reports a synthesis (Scheme 2) in which chroman carboxylic acid is transformed into acyl chloride and is made to react with Meldrum's acid so as to then produce the corresponding alpha-chloroketone in three steps. The alpha-chloroketone is then reduced and cyclized to yield epoxide. The sequence however, which is also known to work on chiral acids R and S, is long and laborious.

Scheme 2

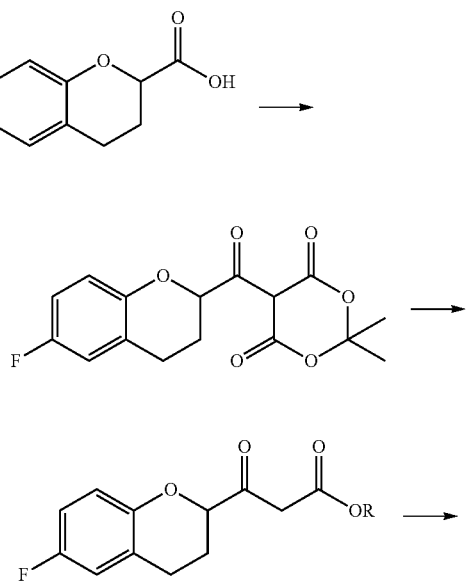

3

-continued

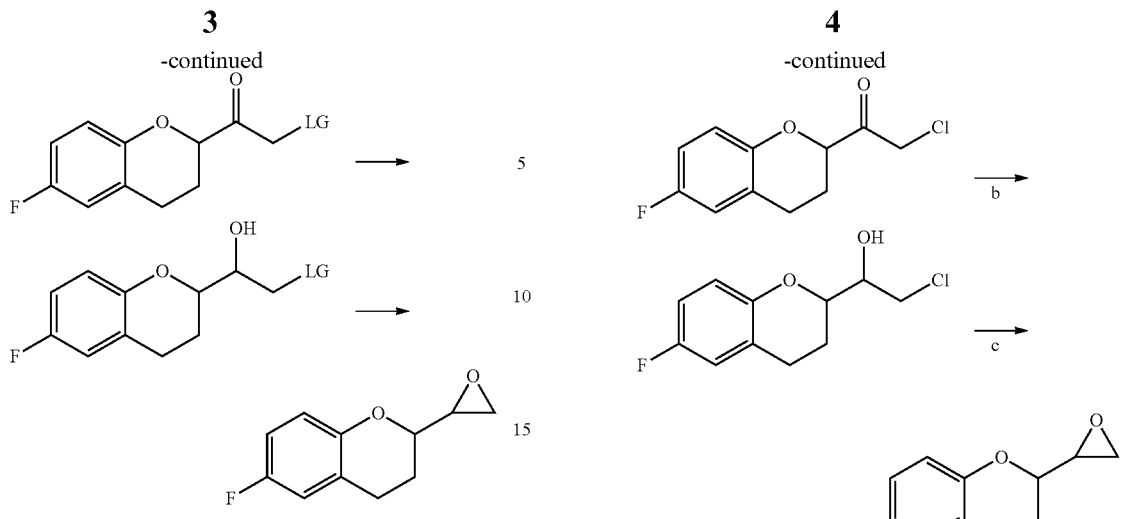

WO2010034927 (Zach System) reports the preparation of epoxides from the corresponding carboxylic esters, both in racemic form and in individual chiral isomers, via the formation of alpha-haloketone (Scheme 3).

Scheme 3

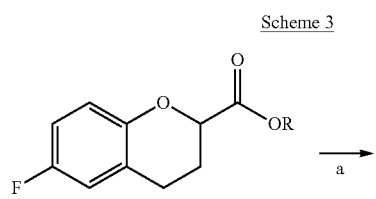

4

-continued a. BuLi, CH$_2$BrCl, -80° C., then AcOH; b. NaBH$_4$, EtOH, 0° C.; c. i-PrOH, NaOH The chroman carboxylic ester is treated at a very low temperature with LiCH$_2$Cl so as to obtain, after quenching with acetic acid, the corresponding alpha-chloroketone, which is then reduced to alpha-chloro alcohol and is cyclized to yield epoxide.

WO2008064826 (Zach System) describes an industrially applicable method which makes it possible to obtain the 4 possible enantiomers of 6-fluoro-chroman epoxide without resorting to chiral chromatography (Scheme 4).

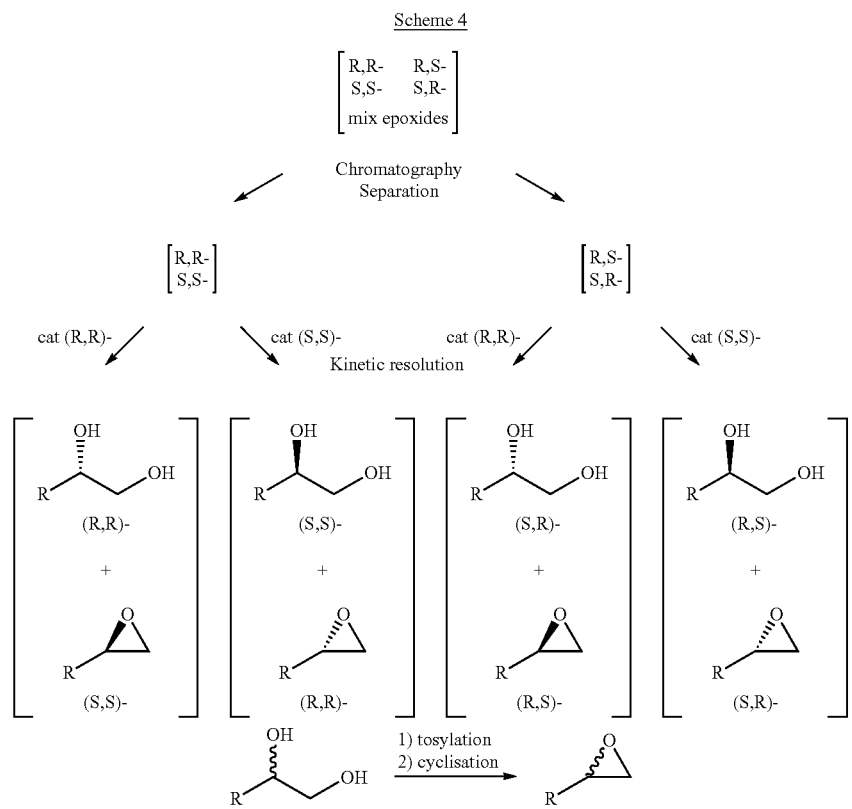

After separation by chromatography of the two diastereomer epoxides (both a racemic mixture), each of the two isomers is subjected to enantioselective opening of the ring in the presence of a chiral catalyst of cobalt. At the end of the process, the unreacted, enatiomerically pure diol and epoxide are easily separated using the methods known in the literature. The diols are reconverted to epoxides via tosylation and cyclization. The synthesis nonetheless still provides chromatographic separation of two diastereoisomers.

WO2011091968 (Corden Pharma) describes a method for obtaining enantiomerically pure chromanyl chloro alcohols by means of enzymatic reduction of the corresponding chloroketones (Scheme 5):

formulas IIa and IIb in a single step and with an increased chemical purity of 96-98%. Such a purity can be brought subsequently to a value greater than 99% (HPLC), after a single crystallization.

In addition, the process comprises a step of enantioselective reduction of the chromanyl haloketones of formulas IIIa and IIIb into haloalcohols of formula IVa-d.

In particular, it has been found that such a reduction occurs with sufficient enrichment into one of the two diastereomers of formula IV if an apolar solvent is used, such as cyclohexane or heptane or methylcyclohexane. This is a particularly surprising aspect insofar as apolar solvents have never been described in the literature as solvents suitable for Scheme 5

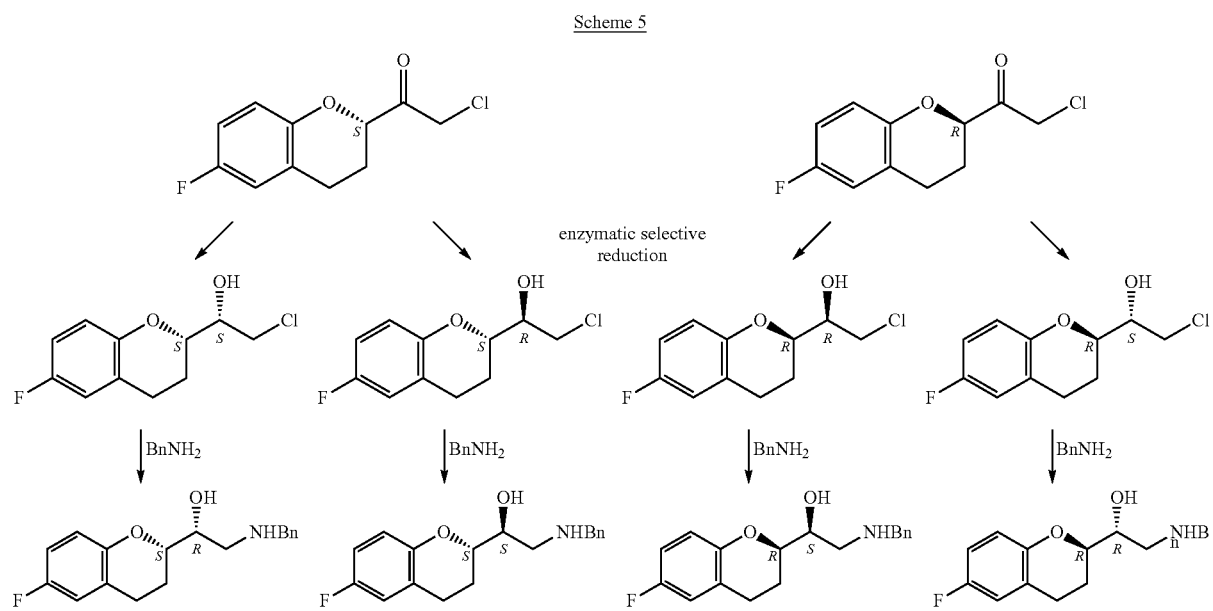

The chloro alcohols thus obtained are developed into the corresponding amino alcohols, without the transition to epoxides, by means of a reaction with basic catalysis. The reaction of the amino alcohols with the appropriate chloro alcohols results in the various isomers of Nebivolol. Such reactions both involve very long times.

SUMMARY OF THE INVENTION

What is described here is a novel efficient process, which is also applicable on an industrial scale, for the synthesis of chromanyl haloketones of formulas IIIa and IIIb and of 6-fluoro-(oxiranyl)chromans of formula Ia-d (epoxide). Such compounds can be used advantageously as intermediates for the synthesis of Nebivolol.

In particular, the process of the invention optimizes the synthesis of the above-mentioned compounds, allowing a reduction of the synthetic steps.

In some cases, the optimization involves an elimination or reduction of steps aimed at the separation of the enantiomers, for example the enantiomeric epoxide pairs (RR/SS RS/SR), and of other diastereoisomeric intermediates.

The process of the invention, in primis, provides an efficient synthesis of chromanyl haloketones of formulas IIIa and IIIb. Such haloketones, which are starting compounds for the synthesis of the epoxides of formula (Ia-d), are synthesized from the corresponding chromanyl esters of oxazaborolidine-catalyzed reductions. In addition, as reported in Table 1 below, solvents normally used in such reductions, namely THF, toluene, and DCM, do not make it possible to obtain an equally high diastereoisomeric excess.

The following thus forms a first subject of the present invention:

a process for the synthesis of chromanyl haloketones of formula IIIa-b as separate isomers or as a racemic mixture

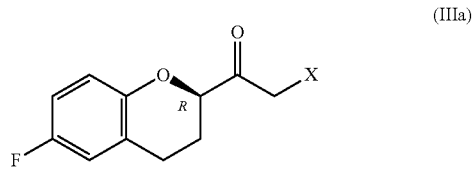
(IIIa)

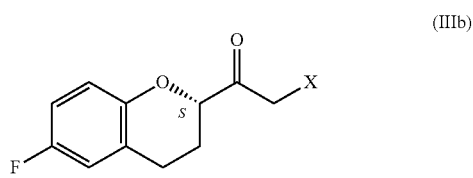
(IIIb)

comprising the following steps:

a. reacting an ester of formula IIa-IIb,

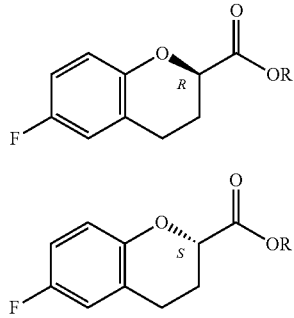
(IIa)

(IIb)

wherein R is a linear $C_1$-$C_6$ alkyl group, in the form of a separate isomer or as a racemic mixture
with a metal-organic compound and a salt of the alpha haloacetic acid of general formula A

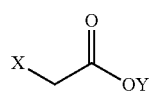
Formula A wherein X is halogen and Y is H, or metal;

b. carrying out an in situ decarboxylation by treatment with an aqueous inorganic acid to give the corresponding chromanyl haloketone of formula IIIa-b in the form of a separate isomer or in racemic form.

The second subject of the invention is formed by the above process comprising the following additional steps in order to obtain the epoxides of formula Ia-Ic in the form of separate optically active isomers

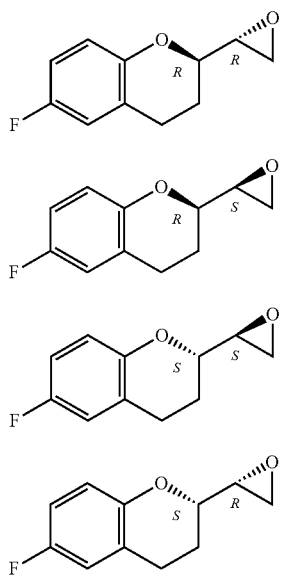
(Ia)

(Ib)

(Ic)

(Id)

c. reducing in an apolar solvent the haloketone of formula IIIa or IIIb

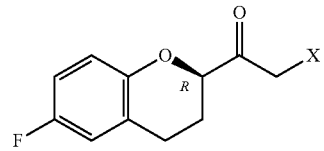
(IIIa)

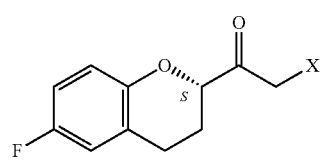
(IIIb)

with a complex of borane in the presence of an oxazaborolidine catalyst (RCBS) of formula B

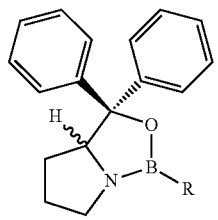
Formula B wherein R=methyl or butyl,
wherein said catalyst has R or S chirality, to obtain the respective haloalcohol of formula IV

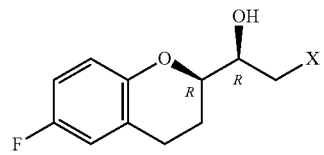
(IVa)

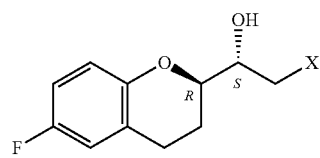
(IVb)

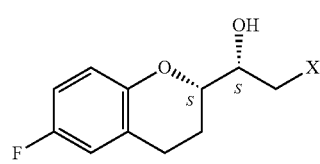
(IVc)

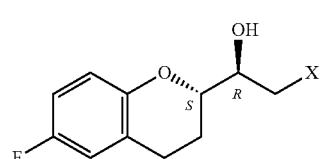
(IVd)

d. carrying out an in situ cyclization of the said alcohol with an aqueous solution of an alkaline base, to give the corresponding epoxides of formula Ia-Id.

A further subject of the invention is formed by the above process comprising additional steps for obtaining benzylamines of formula V, benzylnebivolol of formula VI, and Nebivolol.

The process described here makes it possible to eliminate the disadvantages of the known synthesis pathways used for the synthesis of chromanyl haloketones of formulas IIIa and IIIb and for the synthesis of oxiranylchromans of formula Ia-d, these disadvantages being summarized by:
- length and complexity of the synthesis processes,
- need for chromatographic purification,
- reaction conditions not easily applicable on an industrial scale, such as very low temperatures or instability of intermediates.

The epoxides, which are obtained easily and in industrial quantities in accordance with the process forming the subject of the invention, can be used in the synthesis of the active ingredient Nebivolol.

Further advantages and features of the present invention will become clear from the following detailed description.

DETAILED DESCRIPTION OF THE INVENTION

The present invention describes a process for the synthesis of the intermediates constituted by chromanyl haloketones of formulas IIIa and IIIb and 6-fluoro-2-(oxiran-2-yl) chromans of formula Ia-d (epoxides). Such intermediates can be used in the preparation of Nebivolol in accordance with the following scheme:

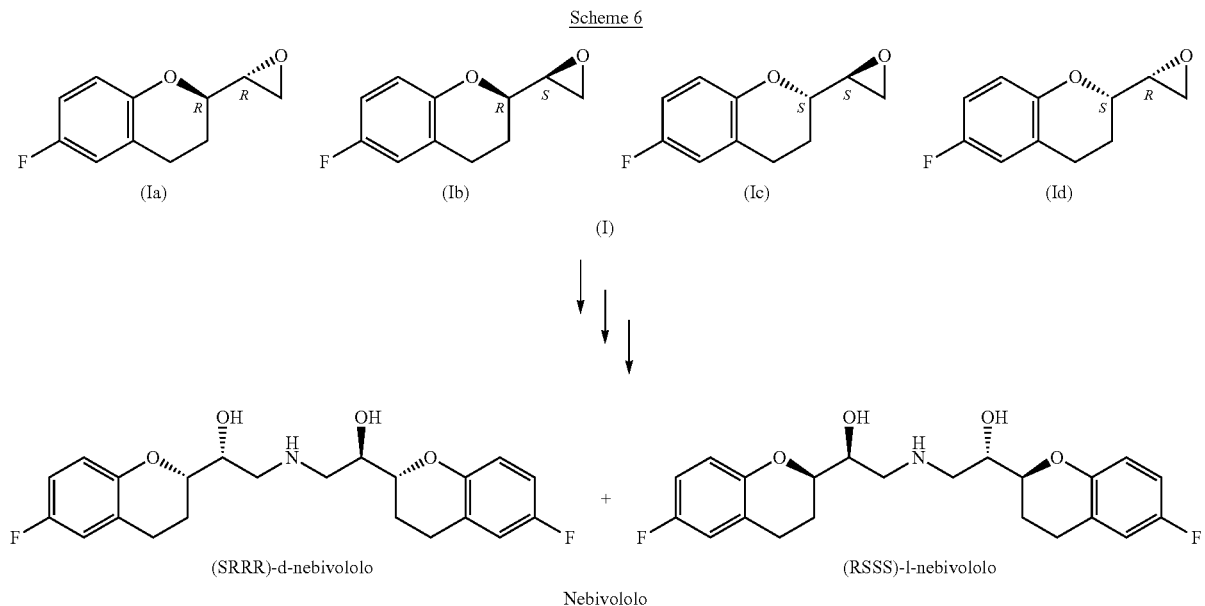

Scheme 6

I Chromanyl haloketones (IIIa-b)

The process for preparing the compounds IIIa-b starting from the esters IIa and b is illustrated in Scheme 7 below.

Scheme 7

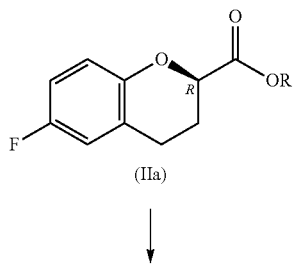

(IIa)

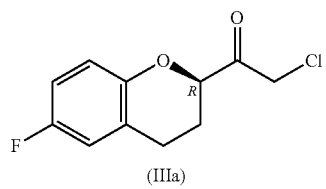

(IIIa)

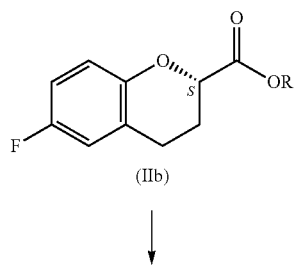

(IIb)

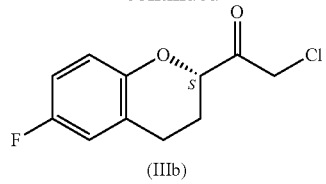

(IIIb)

The starting product is the ester of 6-fluoro-chroman 2-carboxylic acid of formula (IIa) and/or (IIb). Although such an ester can be used in racemic form, for the purposes of the present invention it is preferably used in the form of a pure enantiomer (R) or (S).

The radical R in formula II is a $C_1$-$C_6$ alkyl group, preferably a methyl, ethyl, n-propyl, iso-propyl, or (n-, t-, sec)butyl group. The ester is treated (step a.) with a metal-organic compound in the presence of an alpha-haloacetic acid of general formula A

Formula A

The metal-organic compound can have the formula RMgX, wherein X represents a halogen and R represents a C1-C6 alkyl residue. The alkyl group can be linear or branched, preferably tertiary. For example, such a compound is tert-butylmagnesium chloride (tBuMgCl). Alternatively, the compound can be a magnesium amide. The magnesium amide can be prepared, even at the time of use, from dialkylamine, for example diisopropylamine, and RMgCl, R is an alkyl group.

The alpha-haloacetic acid of formula A can be selected from those acids in which X is a halogen, for example F, Cl, Br, I, and Y is hydrogen (H) or an alkali metal or alkaline earth metal, for example Li, Na, K, Mg. by way of example, the acid can be chloroacetic acid or the salt thereof, i.e. sodium chloroacetate.

The reaction can be carried out by adding the metal-organic reagent, for example tBuMgCl, dropwise to the mixture containing the chromanyl ester (II) and the acid. Alternatively, the metal-organic reagent can be added, again dropwise, simultaneously with the ester (II) and at the same time to a suspension of the acid, so as to maintain a high dilution of ester and metal-organic base throughout the course of the reaction. The temperature is maintained within the range −10/+10° C., preferably between −5/+5° C., or between −3/+3° C.

The synthesis reaction of chromanyl ketones (III) is carried out in inert organic solvent, for example a solvent belonging to the family of the ethers. By way of example, the solvent is tetrahydrofuran, alone or in mixture with methyl tert-butyl ether (MTBE).

The next step (step b.) is a decarboxylation in situ of the formed 2-chloro-3-(6-fluorochroman-2-yl)-3-oxopropanoic intermediate, resulting in the corresponding chromanyl haloketones of formula IIIa or IIIb. These will be in the form of separate enantiomers or a racemic mixture, depending on whether the starting ester is in the form of a separate enantiomer or is in racemic form, respectively. Clearly, if in racemic form, the separate enantiomers of the 6-fluoro chromanyl haloketone of formula IIIa or IIIb can be isolated from the racemic mixture in accordance with any technique considered suitable for this purpose by a person skilled in the art.

An inorganic aqueous acid is then added to the reaction mixture of step (a), preferably slowly and whilst keeping the temperature unchanged, for example −5° C./+5° C., or between −3° C./+3° C., in order to achieve a pH of the mixture that is equal to or less than 5, preferably a pH between 1-3. The acid can be, for example, HCl or NaHSO$_4$. The reaction time in order to obtain directly the haloketones (IIIa-b) is approximately 20 minutes. The mixture is then left under stirring at ambient temperature for at least 30 minutes.

The haloketones IIIa-b are therefore obtained in a single step and with an increased chemical purity of 98%. Such a purity can then be brought to a value greater than 99% (HPLC), after a single crystallisation.

The haloalcohols (IVa-d).

The process described above can comprise an additional step (step c.) of enantioselective reduction of the 6-fluoro chromanyl haloketone of formula IIIa or IIIb so as to obtain the corresponding haloalcohols (IVa-d).

The enantioselective reduction is carried out with an oxazaborolidine catalyst (R-CBS), and with a complex of borane.

The oxaborolidine catalyst has the formula B,

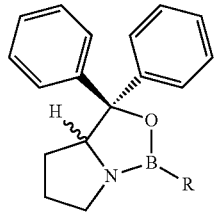

Formula B wherein R=a selection from methyl (Me) or butyl (Bu) to give MeCBS and BuCBS respectively.

The catalyst itself has R or S chirality: R-(R-CBS) or S-(R-CBS).

The reduction reaction is carried out in an apolar solvent. The optimal apolar solvent is selected from cyclohexane, methylcyclohexane, heptane or mixtures thereof. The complex of borane is selected from the group comprising borane-diethylaniline (BH$_3$*DEA), borane-dimethylsulfide (BH$_3$*DMS), borane-tetrahydrofuran (BH$_3$*THF). The complex is preferably BH$_3$*DEA.

The stereoselectivity of the reduction reaction is dependent both on the solvent used and on the R or S chirality of the catalyst. Depending on the chirality of the catalyst, an R or S alcohol will be obtained, respectively. Consequently, the reduction reaction of the chromanyl haloketone (III) will produce the four possible diastereoisomers of the chromanyl alcohol of formula IVa-d in different percentages depending on the conditions adopted. In particular, the enantioselective reaction starting from the (R)chromanyl haloketone IIIa with the catalyst R-(R-CBS) will lead to the formation of the chromanyl haloalcohol of formula IVa, whereas the reaction of the same haloketone IIIa with the catalyst S-(R-CBS) will lead to the formation of the chromanyl haloalcohol of formula IVb. Alternatively, the enantioselective reaction starting from the (S)chromanyl haloketone IIIb with the catalyst R-(R-CBS) will lead to the formation of the chromanyl haloalcohol of formula IVd, whereas the reaction of the same haloketone IIIb with the catalyst S-(R-CBS) will lead to the formation of the chromanyl haloalcohol of formula IVc.

The temperature of the reduction reaction can be between 15° C. and 50° C., for example between 25° C. and 45° C.

At the end of the reaction, the complex of borane can be neutralized with acetone where appropriate.

The reaction as described above leads to the formation of the haloalcohols with a diastereomeric purity at least equal to 90%.

As reported in Table 1, the specific selection of the apolar solvent and the chirality of the catalyst make it possible to obtain diastereomeric mixtures heavily enriched with one of the diastereoisomers of formulas IVa to IVd.

TABLE 1

| N° | III | MeCBS or BuCBS | Diastereomers |
|---|---|---|---|
| 1 | IIIa(R) | S | Ia(RR)/Ib(RS) |
| 2 | IIIb(S) | R | Ic(SS)/Id(SR) |
| 3 | IIIa(R) | R | Ia(RR)/Ib(RS) |
| 4 | IIIb(S) | S | Ic(SS)/Id(SR) |

| N° | Solvent | Diastereomeric excess (Ia/Ib o Ic/Id) |
|---|---|---|
| 1 o 2 | THF | 80/20 |
| | DCM | 85/15 |
| | Toluene | 88/12 |
| | Xylene | 98/2 |
| | Cyclohexane | 98/2 |

TABLE 1-continued

| | Methylcyclohexane | 98/2 |
|---|---|---|
| | Heptane | 96/4 |
| 3 o 4 | THF | 27/73 |
| | DCM | 24/76 |
| | Toluene | 21/79 |
| | Xylene | 18/82 |
| | Cyclohexane | 10/90 |
| | Methylcyclohexane | 10/90 |
| | Heptane | 12/88 |

I Fluoro-oxiranyl chroman

The process described above can comprise an additional step of one-pot intramolecular cyclization (step d.) of the chromanyl haloalcohols of formula IV so as to obtain the epoxides (Ia-d) according to the following scheme:

Scheme 8

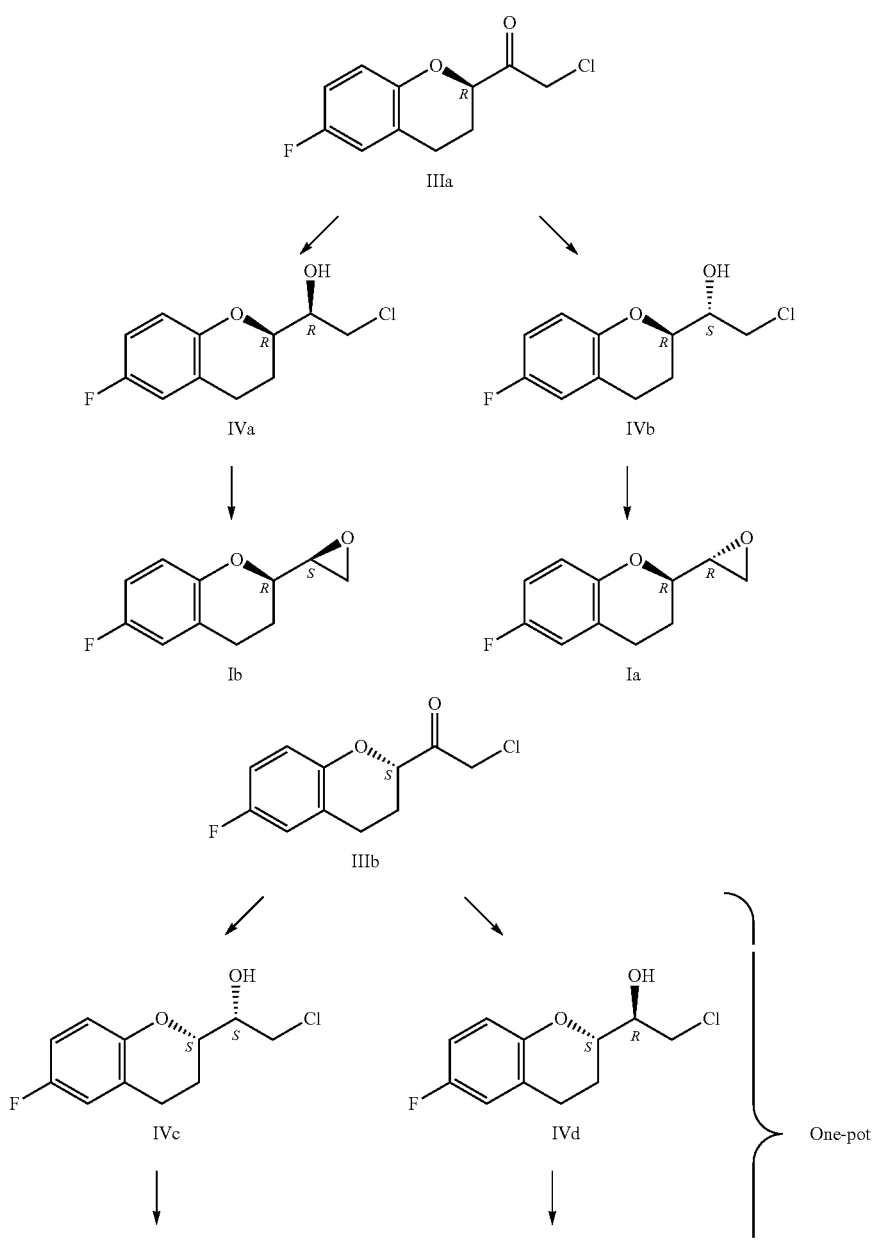

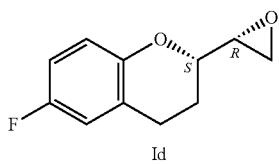
Id

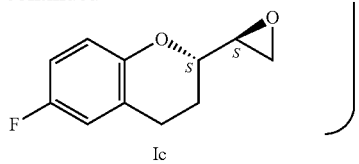
Ic

The cyclization is carried out by adding to the reaction mixture an aqueous solution of an alkaline base, such as NaOH, LiOH or KOH. The base is preferably 50% aqueous.

The base is added at low temperature, for example T=0° C. The mixture thus obtained can then be left at ambient temperature.

The epoxides of formula I obtained as described above are intermediates in the preparation of Nebivolol in the form of a racemic mixture of the two enantioners [2S[2R[R[R]]]] α,α'-[imino-bis (methylene)] bis[6-fluoro-chroman-2-methanol] and [2R[2S[S[S]]]] α,α'-[imino-bis (methylene)] bis[6-fluoro-chroman-2-methanol].

For this purpose, the process described above can be integrated with additional well-known steps, in which the isomer SR of the epoxide (Id) and the isomer RS of the expoxide (Ib) are reacted separately with benzylamine so as to obtain the corresponding benzylamines RS and SR of formula (V)

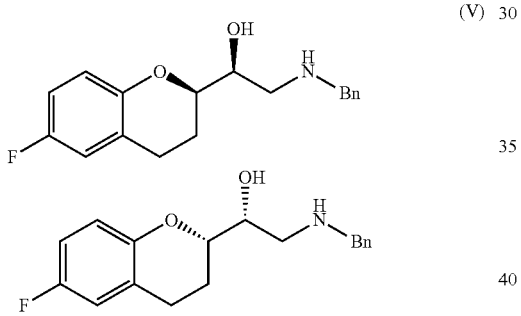
(V)

These amines can then be reacted separately with the chromanyl epoxides of suitable configuration. In particular, the amine (V) RS is reacted with the epoxide SS (Ic), and the amine (V) SR is reacted separately with the epoxide RR (Ia) so as to give, separately, the isomers RSSS and SRRR of the benzylnebivolol of formula VI.

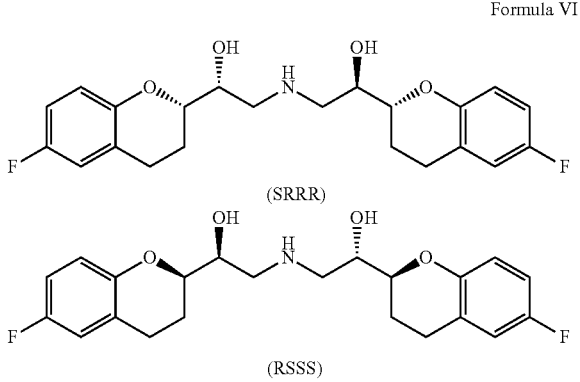
Formula VI
(SRRR)
(RSSS)

The isomer SRRR and the isomer RSSS of benzylnebivolol can then be reunited and crystallised so as to obtain a racemic mixture. The protective benzyl group can then be removed, and the hydrochloride salt can be formed so as to obtain the final product, nebivolol hydrochloride ((SRRR) d-nebivolol+(RSSS) l-nebivolol).

The removal of the benzyl group can be achieved for example by means of catalytic hydrogenation using a catalyst Pd(OH)$_2$. In such conditions the hydrogenation can be carried out in a ratio of acetic acid solvent:water of 7:1.

The hydrochloride salt can be obtained by means of cationic exchange with a solution of NaCl.

EXAMPLES

Example 1

Synthesis of (R)-2-chloro-1-(6-fluorochroman -2-yl) ethan-1-one

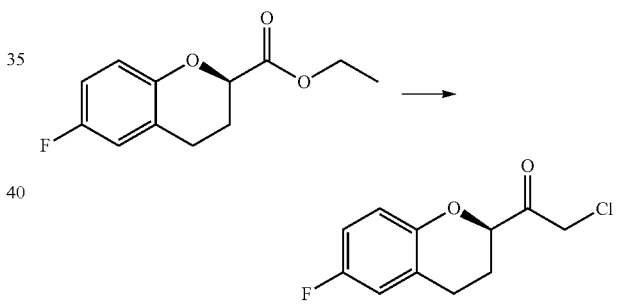

A solution of tBuMgCl 1M in THF (21 l, 21 mol) and a solution containing 1.6 Kg (7.2 mol) of carboxylated (R)-ethyl 6-fluorochromanyl IIa in MTBE (8 L) are added dropwise and at the same time to a sodium chloroacetate suspension (1.74 Kg, 15.1 mol) in MTBE (8 L) at 0° C. in a nitrogen atmosphere. The speeds of dripping of the two solutions are regulated so as to obtain a simultaneous dripping of the two solutions, also ensuring that the temperature remains in the range 3° C./+3° C. during the entire course of the addition (1.5-2.0 hours). At the end of the addition of the reagents, the solution is kept under stirring at a temperature −3° C./+3° C. After confirming that the reaction is complete by means of HPLC analysis, the suspension is added, dropwise, to a mixture composed of a solution of 50% H$_2$SO$_4$ (5.4 Kg), ice (17 Kg) and H$_2$O (17 Kg), and is held at a temperature of −5° C., ensuring that the temperature remains in the range 0° C./+5° C. during the addition. At the end of the addition, it is checked that the pH of the aqueous phase lies within the range pH=1-3, then the solution is brought to ambient temperature, keeping it under stirring for 20 min. The organic phase, which is separated, is treated with 150 mL of NaHCO$_3$ saturated sol. (13.2 Kg), 150 mL of NaHCO$_3$/H$_2$O 1:3 (13.2 Kg), and lastly H$_2$O (13.2 Kg).

The organic phase is concentrated at reduced pressure, three solvent exchanges are performed with isopropanol (360 mL in each case), and then the mixture is crystallized in isopropanol (3.9 Kg, 1.5 volumes), resulting in 1.3 Kg of a solid (79% yield, purity HPLC>99%).

$^1$H NMR (400 MHz, DMSO-d$_6$) δ 6.98-6.90 (m, 2H); 6.90-6.84 (m, 1H), 4.90-4.86 (d, 1H, J=16.0 Hz); 4.89-4.87 (m, 1H); 4.79-4.75 (d, 1H, J=16.0 Hz); 2.88-2.78 (m, 1H); 2.72-2.60 (m, 1H); 2.25-2.10 (m, 1H); 2.08-1.93 (m, 1H).

Example 2

Synthesis of (S)-2-chloro-1-(6-fluorochroman-2-yl) ethan-1-one

The methodology described in Example 1 is applied similarly to the isomer carboxylated (S)-ethyl 6-fluorochromanyl IIb, resulting in an equal yield of the corresponding product (S)-6-fluoro-chromanyl chloroketone IIb.

Example 3

Synthesis of (R)-6-fluoro-2-((S)-oyiran-2-yl)chroman and of (S)-6-fluoro-2-((R)-oxiran-2-yl)chroman cyclohexane (8 Kg) under flow of N$_2$, and the obtained suspension is left under stirring at ambient temperature for 15 minutes. The chloroketones IIIa or IIIb (0.9 Kg, 3.9 mol) are added, respectively, to such a reducing mixture in portions of 45 g/10 minutes. After 20 minutes following the last addition, the HPLC analysis reveals the almost total disappearance of the starting product (6-fluoro-chromanyl chloroketone<0.5%) and the formation to a predominant extent, equal to 90% (enantiomeric purity), of the isomer (R)2-chloro-1-((R)-6-fluorochroman-2-yl)ethan-1-ol (IVa) compared to the isomer (S)2-chloro-1-((R)-6-fluorochroman-2-yl)ethan-1-ol (IVb), or, respectively, in the case of IIIb as starting product, of the isomer (S)2-chloro-1-((S)-6-fluorochroman-2-yl)ethan-1-ol (IVb) compared to (R)2-chloro-1-((S)-6-fluorochroman-2-yl)ethan-1-ol (IVc), depending on the chirality of the used catalyst. Acetone (0.7 Kg) is added in drops slowly to the reaction mixture, cooled to 0-5° C., the temperature is returned to ambient value, and the mixture is left under stirring for 1 hour. After this, an aqueous solution of 50% NaOH (16 Kg) is added, dropwise, to the mixture, cooled to 0° C.-5° C., continuing the stirring at ambient temperature (12-15 hours). After filtration of the mixture, the organic phase is separated, treated with H$_2$SO$_4$ 1M (7.5 Kg), then with H$_2$O (2×8 Kg), and the solvent is removed at reduced pressure so as to obtain, respectively,

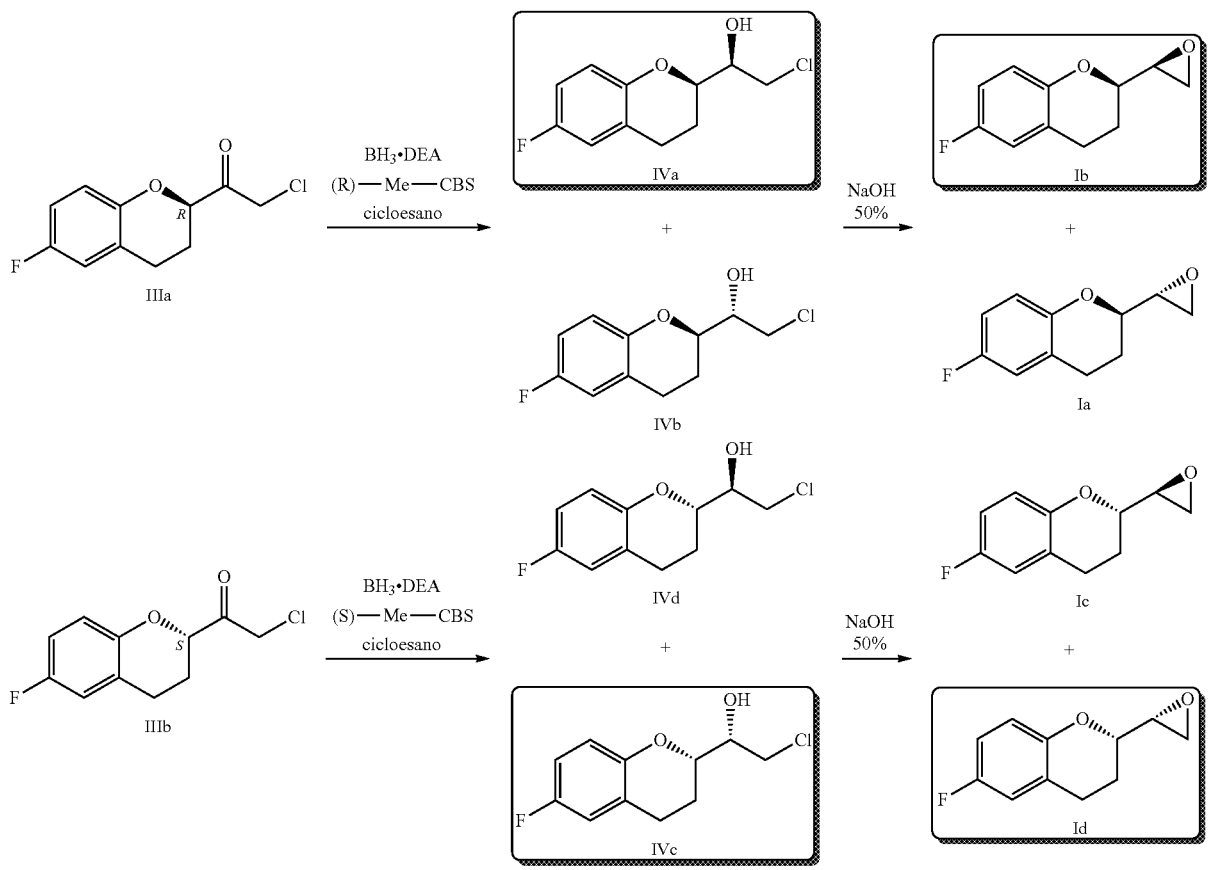

(R)-methyl oxazaborolidine ((R)-MeCBS) or (S)-methyl oxazaborolidine ((S)-MeCBS) (35.9 g, 0.129 mol, 3.3%) is added to a solution of BH$_3$.DEA (0.70 Kg, 4.3 mol) in (R)6-fluoro-2-(S)oxiranyl chroman (Ib) or (S)6-fluoro-2-(R) oxiranyl chroman (Id), with a yield for the two steps equal to 90%.

Example 4

Synthesis of (R)-6-fluoro-2-((R)-oxiran-2-yl)chroman and of (S)-6-fluoro-2-((S)-oxiran-2-yl)chroman

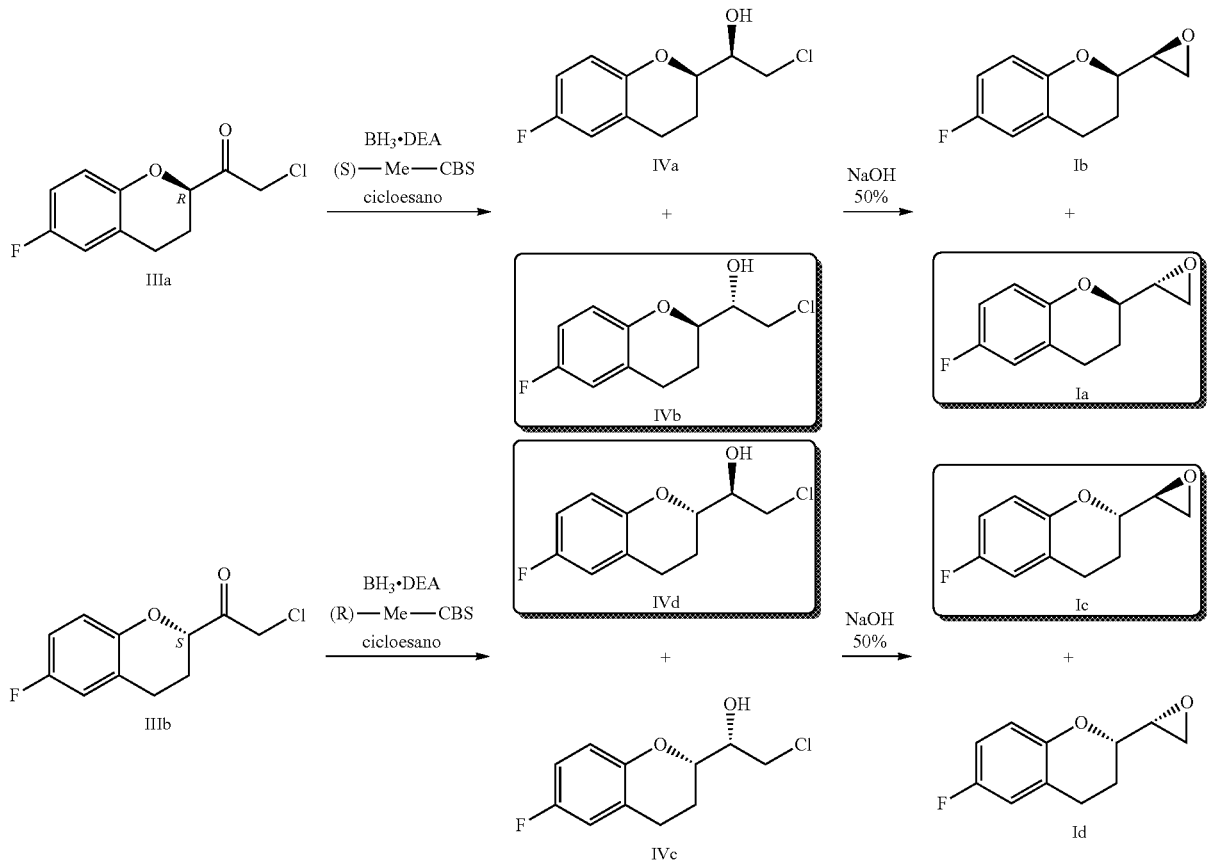

(R)-methyl oxazaborolidine ((R)-MeCBS) or (S)-methyl oxazaborolidine ((S)-MeCBS) (35.9 g, 0.129 mol, 3.3%) is added to a solution of $BH_3.DEA$ (0.70 Kg, 4.3 mol) in cyclohexane (8 Kg), under flow of $N_2$, and the obtained suspension is left under stirring at ambient temperature for 15 minutes. The chloracetone IIIa or IIIb (0.9 Kg, 3.9 mol) is added, respectively, to such a reducing solution in portions of 45 g/10 minutes. After 20 minutes following the last addition, the HPLC analysis reveals the almost total disappearance of the starting product (6-fluoro-chromanyl chloroketone<0.5%) and the formation to a predominant extent, equal to 98% (diastereomeric purity), of (S)2-chloro-1-((R)-6-fluorochroman-2-yl)ethan-1-ol (IVb) compared to the enantiomer (R)2-chloro-1-((R)-6-fluorochroman-2-yl)ethan-1-ol (IVa), or of the isomer (R)2-chloro-1-((S)-6-fluorochroman-2-yl)ethan-1-ol (IVd) compared to the corresponding isomer (S)2-chloro-1-((S)-6-fluorochroman-2-yl)ethan-1-ol (IVc), depending on the chirality of the used catalyst. Acetone (0.7 Kg) is added in drops slowly to the reaction mixture, cooled to 0-5° C., the temperature is returned to ambient value, and the mixture is left under stirring for 1 hour. After this, an aqueous solution of 50% NaOH (16 Kg) is added, dropwise, to the mixture, cooled to 0° C.-5° C., continuing the stirring at ambient temperature (12-15 hours). After filtration of the mixture, the organic phase is separated, treated with $H_2SO_4$ 1M (7.5 Kg), then with $H_2O$ (2×8 Kg), and the solvent is removed at reduced pressure so as to obtain, respectively, (R)6-fluoro-2-((R)-oxiran-2-yl)chroman (Ia) and (S)-6-fluoro-2-((S)-oxiran-2-yl)chroman (Ic), with a yield for the two steps equal to 90%.

Example 5

Synthesis of the Amines Vb RS and Vd SR from the Epoxides Ib RS and Id SR (R)-2-(benzylamino)-1-((S)-6-fluorochroman-2-yl)ethan-1-ol; (S)-2-(benzylamino)-1-((R)-6-fluorochroman-2-yl)ethan-1-ol

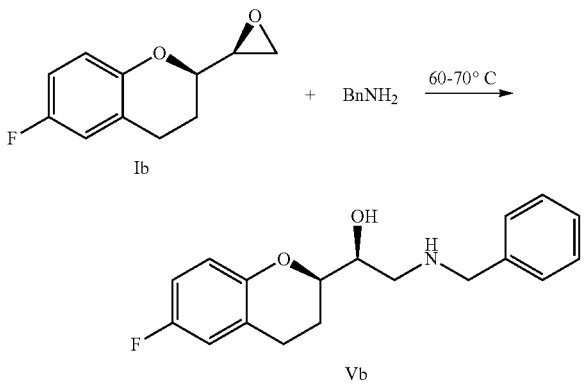

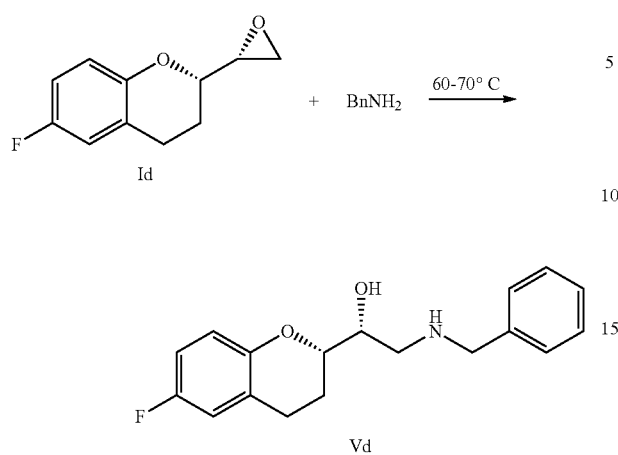

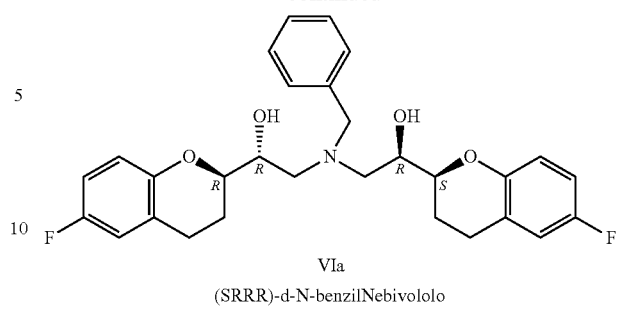

(SRRR)-d-N-benzilNebivololo (R)-2-(benzylamino)-1-((S)-6-fluorochroman-2-yl)ethan-1-ol Vd (0.66 Kg) is added to a solution of the epoxide Ia (0.45 Kg) in absolute ethanol (2.5 L). The suspension is heated to 80-90° C. for 24-48 hours until completion of the reaction (reagents <2%).

The epoxide (Ib) or (Id) (0.68 Kg, 3.5 mol) is suspended in BnNH$_2$ (3.76 Kg). The mixture is heated to 60-70° C. for 2 h (complete solubilization), then the temperature is increased to 90±5° C., with distillation under vacuum of half of the added BnNH$_2$. After cooling to ambient temperature, heptane (6.1 Kg) is added to the reaction mixture, which is left under vigorous stirring, still at ambient temperature, for at least 12 h. The obtained suspension is filtered, and the solid obtained is suspended in cyclohexane (7 Kg), and the suspension is heated under reflux for 30 minutes, then cooled slowly at ambient temperature and left under stirring for 1-2 hours. After filtration and drying in a vacuum oven at 35° C. for at least 8 hours, the (S)-2-(benzylamino)-1-((R)-6-fluorochroman-2-yl)ethan-1-ol Vb and the (R)-2-(benzylamino)-1-((S)-6-fluorochroman-2-yl)ethan-1-ol Vd with a purity>98% (HPLC) and a yield equal to 63% are obtained, respectively, from the chloroketones IIIa and IIIb.

Example 6

Synthesis of (SRRR)-d-N-benzylnebivolol VIa

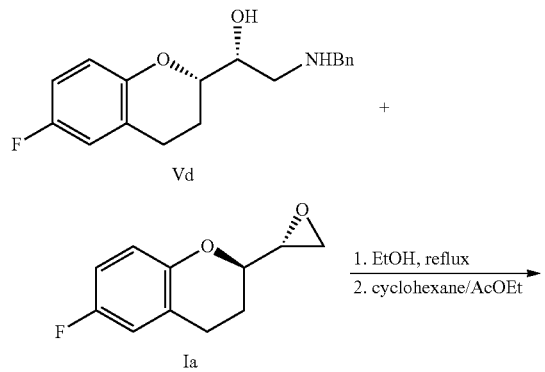

Example 7

Synthesis of (RSSS)-1-N-benzylnebivolol VIb

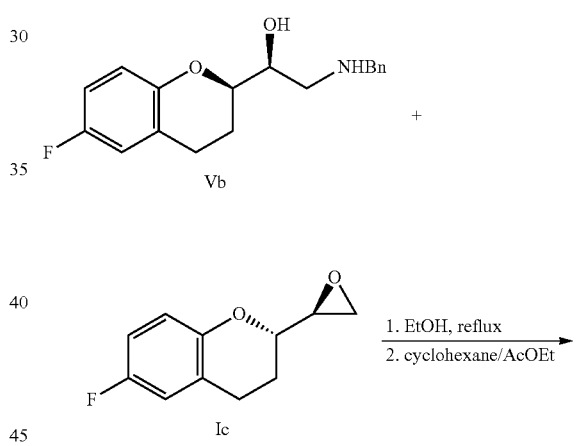

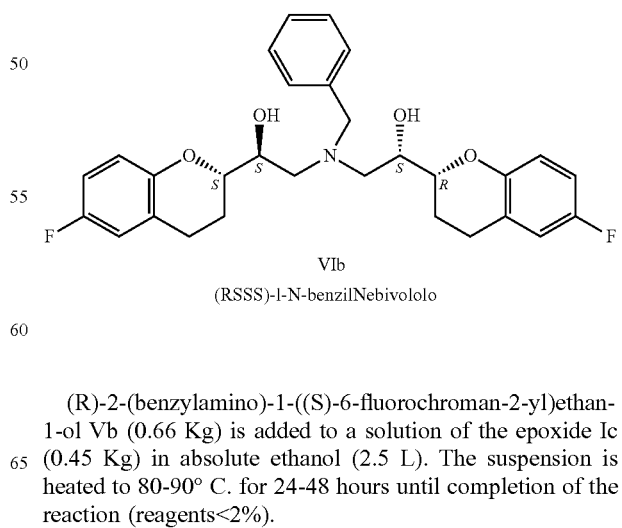

(RSSS)-l-N-benzilNebivololo (R)-2-(benzylamino)-1-((S)-6-fluorochroman-2-yl)ethan-1-ol Vb (0.66 Kg) is added to a solution of the epoxide Ic (0.45 Kg) in absolute ethanol (2.5 L). The suspension is heated to 80-90° C. for 24-48 hours until completion of the reaction (reagents<2%).

Example 8

Synthesis of d,l-benzylnebivolol

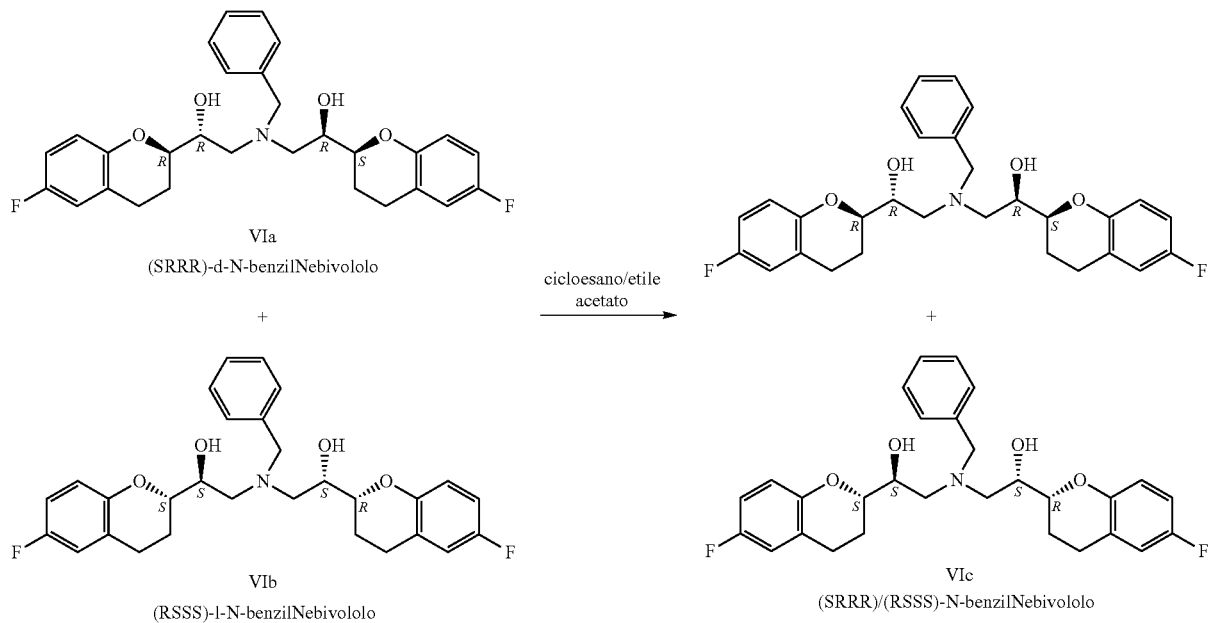

The two mixtures containing the isomers d- and l-N-benzylnebivolol VIa and VIb, obtained respectively as described in Example 6 and in Example 7, are combined and concentrated at reduced pressure. The obtained residue (purity>85%) is crystallized from a mixture 7:1 cyclohexane/EtOAc (12.6 volumes), so as to obtain N-benzylnebivolol VIc (1.77 kg) with a yield equal to 80.5% compared to the amino alcohol VI.

Example 9

Synthesis of Nebivolol Hydrochloride

20% Pd(OH)$_2$/C (50% wet) (approximately 24 g) is added to a suspension of (RSSS)/(SRRR)-N-benzylnebivolol VIc (1.5 Kg) in AcOH (10 Kg) and H$_2$O (1 Kg). The suspension is left under stirring in an H$_2$ atmosphere for approximately 12 hours. At the end of the reaction, the catalyst is filtered off and an aqueous solution of NaCl (1.06 Kg of NaCl in 21 kg of H$_2$O) is added under stirring, with observation of the spontaneous precipitation of a white solid. After stirring for at least 8 hours, the suspension is filtered and the solid is washed with 400 mL of H$_2$O (6 Kg), then with EtOH (3 Kg), so as to obtain the nebivolol hydrochloride as a white solid (1.1 Kg, yield 95%, purity HPLC 99.7%).

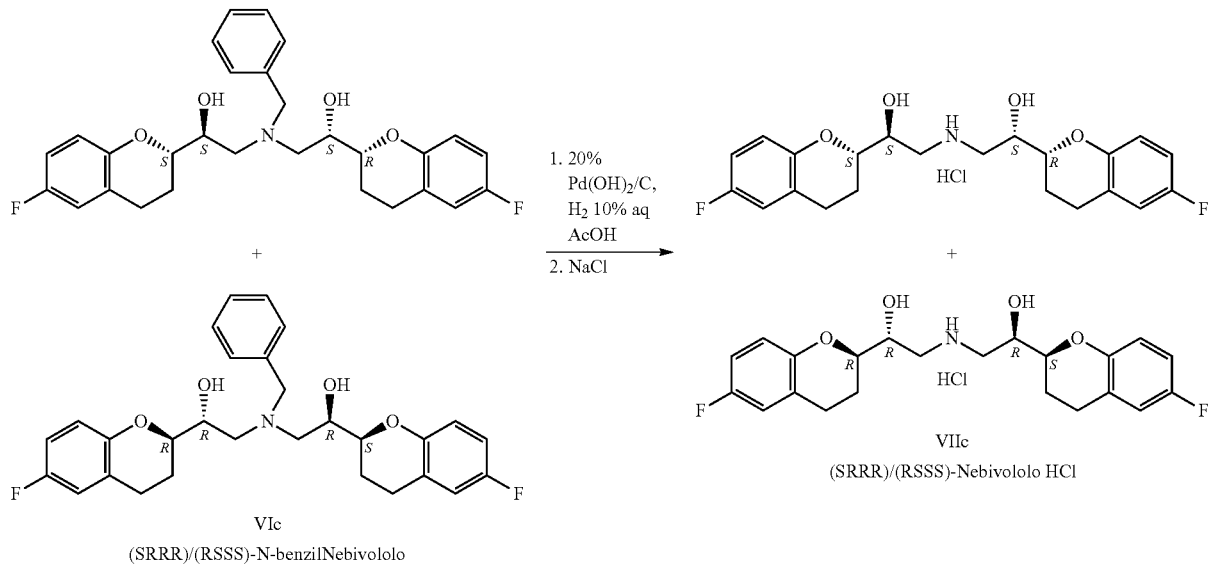

The invention claimed is:

1. A process for the synthesis of chromanyl haloketones of formula IIIa and/or IIIb as separate isomers or as a racemic mixture

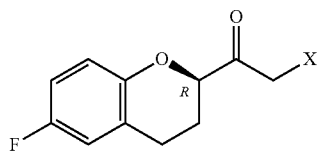
(IIIa)

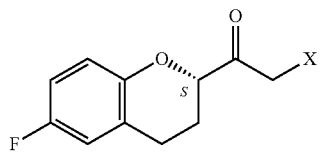
(IIIb)

comprising reacting an ester of formula IIa and/or IIb,

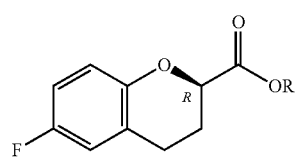
(IIa)

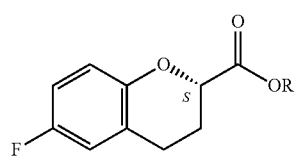
(IIb)

wherein R is a linear $C_1$-$C_6$ alkyl group, in a form of a separate isomer or as a racemic mixture with a metal-organic compound and a salt of a haloacetic acid of general formula A

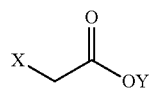
Formula A wherein X is F, Cl, Br, or I and Y=H, Li, Na, K, or Mg;
wherein the reacting of the ester with the metal-organic compound is carried out at a temperature between −10° C. and +10° C.,
wherein the metal-organic compound is an organic magnesium compound of formula RMgX, where X is a halogen and R is an amine or a linear or branched, $C_1$-$C_6$ alkyl residue; and
in situ decarboxylating in the presence of an aqueous inorganic acid until the reaction reaches a pH equal to or less than 5, to result in the corresponding chromanyl haloketone of formula IIIa and/or IIIb in the form of a separate isomer or in racemic form.

2. The process according to claim 1, wherein the metal-organic compound is t-BuMgCl.

3. The process according to claim 1, wherein the haloacetic acid is chloroacetic acid or a sodium salt thereof.

4. The process according to claim 1, wherein the reacting of the ester with the metal-organic compound is carried out at a temperature between −5° C. and +5° C., or between −3° C. and +3° C.

5. The process according to claim 1, wherein the solvent used in the reacting of the ester with the metal-organic compound is an ether, wherein the ether is tetrahydrofuran, methyl tert-butylether, or mixtures thereof.

6. The process according to claim 1, further comprising reducing a chromanyl haloketone of formula IIIa or IIIb in an apolar solvent, wherein the formula IIIa or IIIb are

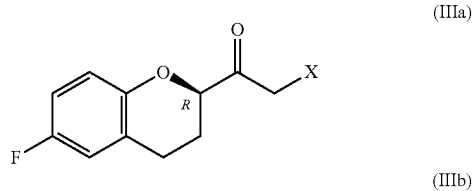
(IIIa)

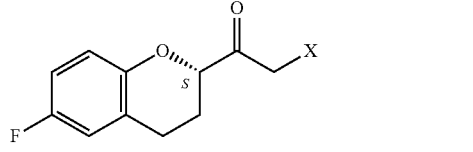
(IIIb)

with a complex of borane in the presence of an oxazaborolidine catalyst (RCBS) of formula B

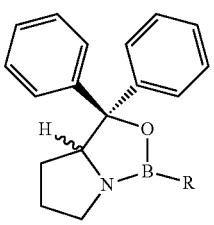
Formula B wherein R=methyl or butyl,
wherein the catalyst has R or S chirality,
to obtain the respective haloalcohol of formula IV

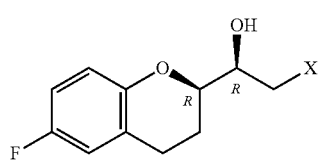
(IVa)

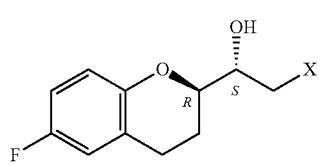
(IVb)

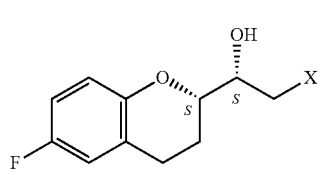
(IVc)

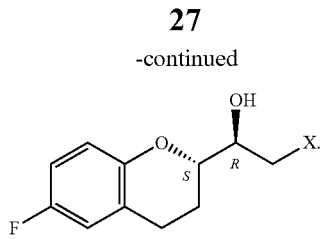
(IVd)

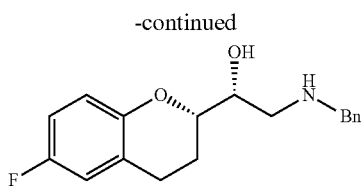
(Vd... continued)

7. The process according to claim 6, wherein the apolar solvent is cyclohexane, methylcyclohexane, or heptane.

8. The process according to claim 6, wherein the catalyst is (R)MeCBS or (S)MeCBS.

9. The process according to claim 6, wherein the catalyst is (R)BuCBS or (S)BuCBS.

10. The process according to claim 6, wherein the complex of the borane is borane-diethylaniline (DEA*BH3), borane-dimethylsulfide (BH3*DMS), or borane-tetrahydrofuran (BH3*THF).

11. The process according to claim 6, further comprising carrying out an in situ cyclization of the haloalcohol with an aqueous solution of an alkaline base, to give the corresponding epoxides of formula Ia-Id in the form of separate optically active isomers:

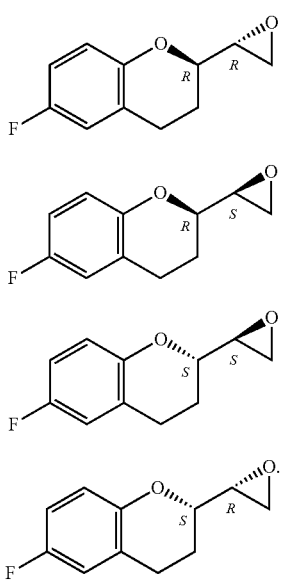
(Ia)
(Ib)
(Ic)
(Id)

12. The process according to claim 11, wherein the alkaline base is a NaOH, LiOH, or KOH solution.

13. The process according to claim 11, further comprising reacting separately the SR isomer of the epoxide (Id) and the RS isomer of the epoxide (Ib) with the benzylamine to obtain the RS and SR benzylammine of formula (V)

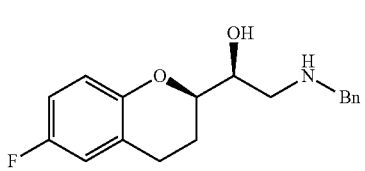
(V)

14. The process according to claim 13, further comprising reacting separately the RS amine (V) with the SS epoxide (Ic) and the amine SR (V) with the epoxide RR (Ia) to give separately the SSSR and SRRR isomers of benzylnebivolol of formula (VI)

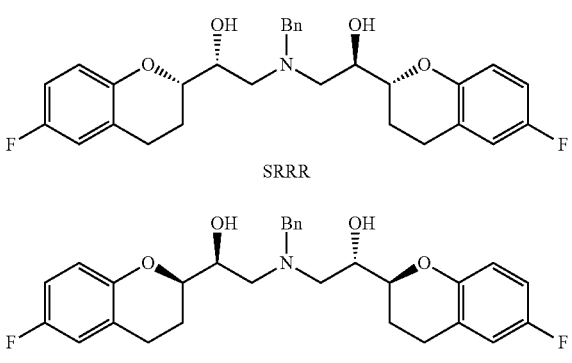
SRRR

RSSS
(VI)

15. The process according to claim 14, further comprising combining the solutions of RSSS and SRRR isomers of benzylnebivolol of formula (VI), and carrying out a crystallization to obtain the SRRR/RSSS benzylnebivolol as a raceme.

16. The process according to claim 15, wherein the crystallization is carried out with a ethyl acetate/cyclohexane mixture and eventual trituration in hot cyclohexane.

17. The process according to claim 15, further comprising removing the benzyl protecting group and forming the hydrochloride salt, to obtain the product Nebivolol hydrochloride.

18. The process according to claim 17, wherein removing the benzyl protecting group comprises removing by catalytic hydrogenation with Pd(OH)$_2$ catalyst.

19. The process according to claim 18, wherein a solvent of the catalytic hydrogenation is acetic acid water 7:1.

20. The process according to claim 16, wherein the crystallization results in a hydrochloride salt that is obtained by cation exchange with NaCl solution.

21. The process according to claim 1, wherein R is a branched $C_1$-$C_6$ alkyl.

22. The process according to claim 21, wherein the branched $C_1$-$C_6$ alkyl is a tertiary alkyl.

* * * * *